United States Patent [19]

Canale

[11] 4,085,752
[45] Apr. 25, 1978

[54] COLOSTOMY BAG PAD

[76] Inventor: James Canale, c/o General Delivery, Collins Ct., Eastport, N.Y. 11941

[21] Appl. No.: 684,120

[22] Filed: May 7, 1976

[51] Int. Cl.² .............................................. A61F 5/44
[52] U.S. Cl. .................................... 128/283; 128/155
[58] Field of Search .............. 128/283, 284, 286, 287, 128/290, 292, 296, 155, 156, 158

[56] References Cited

U.S. PATENT DOCUMENTS

| 2,618,265 | 11/1952 | Adams et al. | 128/283 |
| 3,286,713 | 11/1966 | Kurtz et al. | 128/DIG. 26 |
| 3,422,817 | 1/1969 | Mishkin et al. | 128/DIG. 26 |
| 3,773,048 | 11/1973 | Kirkliauskas | 128/283 |
| 3,799,167 | 3/1974 | Miller et al. | 128/287 |
| 3,895,629 | 7/1975 | Snyder | 128/DIG. 26 |

Primary Examiner—Robert W. Michell
Assistant Examiner—Henry S. Layton
Attorney, Agent, or Firm—Robert D. Farkas

[57] ABSTRACT

A colostomy bag pad that is adapted to be interposed between the bag and the external surface of the abdominal wall and provides an aperture for communication with the external projection of the stoma.

7 Claims, 6 Drawing Figures

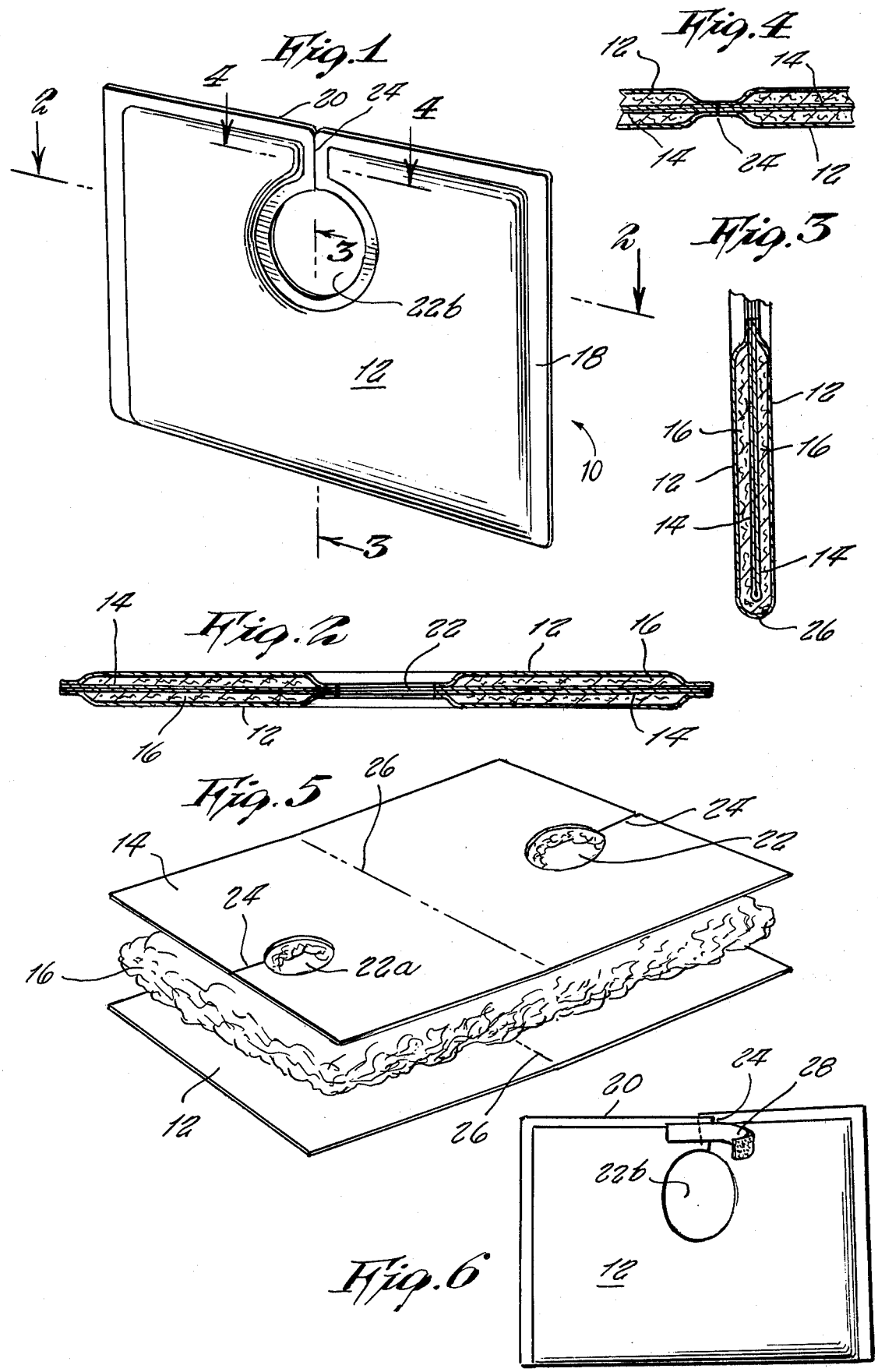

COLOSTOMY BAG PAD

BACKGROUND OF THE INVENTION

This invention relates to a colostomy bag pad; more particularly, to a pad that is adapted to separate the body fluids from the waste fluids and thereby substantially reduce skin irritation around the stoma.

The prior art teaches a variety of colostomy appliances, for example, as disclosed in U.S. Pat. Nos.: 2,546,779; 2,679,248; 2,684,675; 2,814,295; 2,896,625; 3,125,093; 3,695,268; 3,805,789; 3,826,262; and others. None of the foregoing, however, provide for a simple yet effective means of absorbing fluid adjacent the colostomy appliance.

SUMMARY OF THE INVENTION

It is accordingly an object of the instant invention to provide for a new and improved colostomy bag pad.

It is another object of the invention to provide for the same at relatively little cost thereby making it generally available.

It is a further object to provide for a pad that is easily and simply applied.

These and other objects and advantages of the invention will become more apparent from the following detailed disclosure and claims and by reference to the accompanying drawings, in which:

FIG. 1 is a perspective view;

FIG. 2 is a sectional view taken along the line 2—2 of FIG. 1;

FIG. 3 is a side sectional view taken along the line 3—3 of FIG. 1;

FIG. 4 is a sectional view taken along the line 4—4 of FIG. 1;

FIG. 5 is an exploded perspective view; and

FIG. 6 is a front elevational view.

Broadly speaking, the instant invention includes the provision of a colostomy bag pad adapted to be interposed between the colostomy bag and the stoma, comprising a laminate including two opposing sides formed of at least one layer of a liquid permeable sheet, at least one layer of a liquid impermeable sheet disposed in opposing relation between the two opposing sides, a liquid absorbent substance sandwiched between the liquid permeable and liquid impermeable layers, the laminate defining an aperture communicating with both of the layers and the member and a slit communicating between the aperture and one lateral edge of the laminate.

DETAILED DISCLOSURE

Referring more particularly to the drawings, there is shown a substantially rectangular or square shaped member 10, though the shape may vary. The member 10 is comprised of a laminate or composite of a plurality of heterogenious or differing layers. The outer layer 12 is comprised of a liquid and air permeable sheet, i.e., a non woven that is non absorbent yet permits fluid to pass therethrough. The layer 12 may be a single or multiple layer of sheets preferably non-allergenic. Disposed in opposing relation thereto is a layer 14 of a liquid impermeable, yet preferably air permeable sheet like material, such as a plastic layer. Disposed therebetween, there will be further member 16 that is liquid absorbent, such as cotton, wadding, suitable woven and non-wovens and the like. In the preferred embodiment, the lateral edges of the laminate will be sealed (i.e., heat, aqueous insoluble adhesives) such that the liquid that passes through sheet 12 is trapped in the member 16 and cannot leak out therefrom. It is sometimes preferable that the sizes of layers 12 and 14 not be same, such as where layer 14 is larger and is sealed against the outer flap 18 defined by the excess portion of layer 16. In this instance, or the other, it also may be preferable, that the layer 12 be tucked in under itself such that a lip or second flap is formed enveloping the edges of member 16 and which flap is disposed between the underside portion of layer 14 and one underside portion of member 16. The foregoing may in certain instances alleviate leakage problems.

Adjacent each of the lateral edges or longer sides 20 of the laminate 10 there will be defined a substantially spherical aperture 22, 22a that is generally about 1⅜ inches in diameter. The edge 20 defining the same will be about 9 inches in length. Each of the apertures 22, 22a will communicate with the edge 20 by a slit 24 that is substantially perpendicular to the edge and positioned to bisect the aperture 22, or 22a. The aperture is ideally disposed about 1½ inches from the edge; the shorter side of the laminate is generally about 5½ inches. The laminate is used by folding the same about an imaginary fold line 26 disposed transverse the laminate 10. In this instance, the laminate 10 comprises two approximately equal sized and shaped halves that are positioned in opposing relationship such that the apertures 22, 22a are coaxially aligned to form a single aperture 22b. As is apparent, the layer 14 is folded upon itself while the layer 12 forms the complete outer shell with the member 16 disposed between the layers 12 and 14.

In certain embodiments it may be desirable to have closure means 28 such as adhesive tape, pins, etc., communicating between the free edges formed by the slits 24 on each side of the layer 14, such that the diameter defined by the aperture 22, 22a may be adjusted, i.e., larger or smaller depending upon the colostomy appliance.

As is apparent, the laminate is adapted to absorb fluids through the permeable layer 12, from both the colostomy appliance engaging one side thereof and from the stoma engaging the other side thereof. The fluid is then trapped in the member 16 and cannot communicate with the opposing section of the laminate due to the layer 14 blocking the passage.

Since it is obvious that numerous changes and modifications can be made in the above-described details without departing from the spirit and nature of the invention, it is to be understood that all such changes and modifications are included within the scope of the invention.

I claim:

1. A colostomy bag pad adapted to be interposed between the colostomy bag and the stoma, comprising a laminate including two opposing sides formed of at least one layer of a liquid permeable sheet, at least one layer of a liquid impermeable sheet disposed in opposing relation between said two opposing sides, a liquid absorbent substance sandwiched between said liquid permeable and liquid impermeable layers, said laminate having an aperture therein and a slit communicating between said aperture and one lateral edge of said laminate, wherein each of said layers is formed of a single sheet folded substantially in half to form said laminate.

2. The pad as defined in claim 1 wherein said liquid permeable layer is a non-woven.

3. The pad is defined in claim 1 wherein said liquid impermeable layer is a plastic sheet.

4. The pad as defined in claim 1 wherein said liquid absorbent substance is cotton wadding.

5. The pad as defined in claim 1 wherein said slit defines free edges and connecting means adapted to communicate between said free edges formed by said slit and thereby adjust the size of said aperture.

6. The pad as defined in claim 1 wherein the edges of said laminate are sealed to reduce fluid leakage.

7. The pad as defined in claim 1 wherein said layers are of equal size.

* * * * *